(12) United States Patent
Masuda et al.

(10) Patent No.: US 7,931,687 B2
(45) Date of Patent: Apr. 26, 2011

(54) TISSUE ENGINEERED OSTEOCHONDRAL IMPLANT

(75) Inventors: Koichi Masuda, Wilmette, IL (US); Michael J. Hejna, Riverside, IL (US); Brian E. Pfister, Wilmette, IL (US)

(73) Assignees: Articular Engineering, LLC, Northbrook, IL (US); Rush University Medical Center, Chicago, IL (US)

( * ) Notice: Subject to any disclaimer, the term of this patent is extended or adjusted under 35 U.S.C. 154(b) by 1200 days.

(21) Appl. No.: 10/435,883

(22) Filed: May 12, 2003

(65) Prior Publication Data

US 2003/0229400 A1 Dec. 11, 2003

Related U.S. Application Data

(60) Provisional application No. 60/379,933, filed on May 13, 2002.

(51) Int. Cl.
*A61F 2/02* (2006.01)
(52) U.S. Cl. ...... 623/11.11; 623/901; 435/382; 435/395; 424/93.7; 424/422; 424/423
(58) Field of Classification Search ............ None
See application file for complete search history.

(56) References Cited

U.S. PATENT DOCUMENTS

| | | | |
|---|---|---|---|
| 4,642,120 A | 2/1987 | Nevo et al. ............ 623/16 |
| 5,197,985 A | 3/1993 | Caplan et al. ............ 623/16 |
| 5,684,061 A | 11/1997 | Ohnishi et al. ............ 523/114 |
| 5,904,716 A | 5/1999 | Gendler ............ 623/11 |
| 6,077,989 A | 6/2000 | Kandel et al. ............ 623/16 |
| 6,187,329 B1 * | 2/2001 | Agrawal et al. ............ 424/426 |
| 6,197,061 B1 | 3/2001 | Masuda et al. ............ 623/11.11 |
| 6,214,369 B1 | 4/2001 | Grande et al. ............ 424/423 |
| 6,277,151 B1 | 8/2001 | Lee et al. ............ 623/23.61 |
| 6,306,169 B1 | 10/2001 | Lee et al. ............ 623/11.11 |
| 6,335,029 B1 * | 1/2002 | Kamath et al. ............ 424/423 |
| 6,454,811 B1 * | 9/2002 | Sherwood et al. ............ 623/23.76 |
| 2002/0028493 A1 | 3/2002 | De Bruijn et al. ............ 435/174 |

FOREIGN PATENT DOCUMENTS

| | | |
|---|---|---|
| WO | WO 98/16209 | 4/1998 |
| WO | WO 98/40111 | 9/1998 |
| WO | WO 01/29189 | 4/2001 |

OTHER PUBLICATIONS

Schaefer et al, Biomaterials, 2000; vol. 21, pp. 2599-2606.*
Kreklau et al, Biomaterials, 1999; vol. 20, pp. 1743-1749.*
van Susante et al, Biomaterials, 1998, vol. 19, pp. 2367-2374.*
Tampieri et al, "Porosity-graded hydroxyapatite ceramics to replace natural bone" Biomaterials, 2001, vol. 22, pp. 1365-1370.*
Freshney, "Cloning and Selection of Specific Cell Types" (Chapter 11), and "Physical Methods of Cell Separation" (Chapter 12), *Culture of Animal Cells*, A Manual of Basic Techniques, $2^{nd}$ ed., pp. 137-168 (1987.
Klagsbrun, "Large-Scale Preparation of Chondrocytes", *Methods in Enzymology*, 58:560-564 (1979).
Mizrahi, et al., "The 'Instantaneous' Deformation of Cartilage: Effects of Collagen Fiber Orientation and Osmotic Stress", *Biorheology*, 23: 311-330 (1986).
Wakitani, et al., "Mesenchymal Cell-Based Repair of Large, Full-Thickness Defects of Articular Cartilage", *The Journal of Bone and Joint Surgery*, 76: 579-591 (1994).

* cited by examiner

*Primary Examiner* — Allison Ford
(74) *Attorney, Agent, or Firm* — Sonia K. Guterman; Michael I. Falkoff; Teofilo Javier, Jr.

(57) ABSTRACT

Compositions, methods of production and use, and kits for an osteochondral graft involving both articular cartilage and underlying bone are provided.

28 Claims, 3 Drawing Sheets

TISSUE ENGINEERED OSTEOCHONDRAL IMPLANT

RELATED APPLICATION

This application claims the benefit of U.S. provisional application no. 60/379,933, filed May 13, 2002 in the U.S. Patent and Trademark Office, and which is hereby incorporated herein in its entirety.

FIELD OF INVENTION

The present invention relates to compositions for and methods of production of an osteochondral tissue graft comprising both articular cartilage and underlying bone, and methods for surgical implantation of the compositions into human joints for the purpose of filling defects, or replacing damaged or degraded cartilage and bone, and kits having such a graft.

BACKGROUND OF THE INVENTION

Healthy human joint surfaces are covered by articular cartilage, which provides a resilient, durable surface with low friction, for distribution of mechanical forces and protection of the underlying bone. Cartilage is an avascular tissue, having a small number of chondrocytes encapsulated within an extensive extracellular matrix. Damage to the articular cartilage, subchondral bone, or both can result from traumatic injury or a disease state.

There are significant differences in the ability of natural tissues to respond in vivo to different types of injury or disease. Injuries that do not penetrate subchondral bone are associated with a limited repair response. In contrast, osteochondral injuries in which the subchondral bone is penetrated can participate in a repair response due to the influx of reparative cells from the bone marrow. Formation of fibrocartilage, a mixture of hyaline cartilage and fibrous tissue, characterizes the repair response. Fibrocartilage lacks the durability or mechanical properties of normal articular cartilage, and eventually degrades from normal joint use. Many osteochondral injuries become clinically asymptomatic for a period of several years as a result of fibrocartilage formation. Secondary degeneration at the site of the injury can ultimately result in poor joint function, pain, and disability.

Osteochondral grafting has been used to repair or replace articular cartilage and the underlying bone. In osteochondral grafting, cartilage is harvested with the corresponding subchondral bone from a region of less strain, and the cartilage and bone tissue of the defect site is removed by milling, to create a bore of a precise geometry. The harvested tissue is then implanted into the defect site. Healing of the graft bone to the host bone results in fixation of the graft to the host. Larger defects are repaired with several bores, in a procedure termed mosaic plasty. The potential for donor site morbidity, produced by harvest of the autologous graft, however, presents a major remaining disadvantage. Further, potential donor site morbidity limits effective treatment of a defect to a greater extent as the size of the defect increases.

There continues to be a need for an osteochondral implant that can restore normal joint function, and that addresses the limitations of current osteochondral graft technology.

SUMMARY OF THE INVENTION

An aspect of the invention features a transplantable osteochondral implant comprising engineered cartilage tissue attached to a biocompatible support scaffold comprising a plurality of pores. The cartilage tissue is derived from chondrogenic cells cultured in vitro, and the cells have a cell associated matrix (CM). The scaffold contains at least one of natural cancellous bone, demineralized natural cancellous bone, collagen, and bone substitute material. The cells cultured in vitro are recovered with a cell-associated matrix. The cells can be cultured in vitro in alginate beads prior to their introduction to the scaffold material.

The bone substitute material is at least one of calcium phosphate or hydroxyapatite, and has a thickness of at least about 2 mm. For example, the thickness of the support scaffold can be at least about 3 mm, at least about 5 mm, at least about 8 mm, at least about 10 mm or even greater, depending upon the anatomy of the joint into which the implant will be surgically inserted. Further, the CM includes at least one of aggrecan, collagen types II, IX and XI, and hyaluronan. The cartilage tissue comprises at least about 5 mg/cm$^3$ aggrecan, for example, at least about 7 mg/cm$^3$ aggrecan or at least about 10 mg/cm$^3$ aggrecan, and the ratio of aggrecan to hyaluronan in the tissue is about 10:1 to about 500:1. The ratio of aggrecan to collagen is about 1:10 to about 10:1, as is appropriate to tissues cultured for different lengths of time. In an embodiment of the implants, pores of the biocompatible support scaffold include a biocompatible filler agent. The biocompatible filler agent can contain at least one of purified hyaluronan, collagen, or alginate. Alternatively, the pores of the bone substitute material are sufficiently small as to retard growth of chondrogenic cells into the scaffold during the culture process. In alternative embodiments, the scaffold material comprises a gradient of pore sizes, for example, the scaffold material has a larger pore size at the bottom (distal to the top surface of the implant) than at the top, to improve the biomechanical properties of the implant with respect to the surrounding tissues in vivo following implantation. Further, the pores of the porous biocompatible support scaffold in any of the above embodiments include culture medium.

The implant has an exterior surface distal from the underlying scaffold, and the chondrogenic cells and CM are substantially associated with the exterior surface. The cells within the scaffold material are located in a layer of less than about 1 mm from the exterior surface, or in a layer of less than about 2 mm from the surface, i.e., the cells are not uniformly distributed throughout the scaffold, but are predominantly associated a layer that is proximal to the exterior surface. The implant, further can have a removable semi-permeable membrane filter.

Chondrogenic cells can come from a variety of sources. The chondrogenic cells are in general isolated from an articular cartilage or a fibrocartilage. Further, chondrogenic cells can be differentiated chondrocytes or chondrogenic stem cells. The stem cells are from a tissue such as placenta, umbilical cord, bone marrow, skin, muscle, fat, periosteum, and perichondrium. Chondrogenic cells from a fibrocartilage can be obtained from costal, nasal, auricular, tracheal, epiglottic, thyroid, arytenoid and cricoid cartilages. Alternatively, cells from fibrocartilage can be obtained from tendon, ligament, meniscus and intervertebral disc.

An aspect of the invention is a method for producing in vitro a transplantable osteochondral implant. The method involves culturing isolated chondrogenic cells in a culture medium for an amount of time effective for formation of a chondrogenic cell-associated matrix (CM); and contacting a porous biocompatible support scaffold with the chondrogenic cells with CM in the presence of a growth factor for a time effective for forming a resulting engineered cartilage tissue and attaching the engineered cartilage tissue to the biocompatible support scaffold.

In some embodiments, the method further includes, prior to contacting the scaffold, filling pores of the scaffold with a biocompatible filler agent. Filling the pores prevents growth of the overlying cells into the scaffold material beyond a limited depth. Filling the pores comprises using positive pressure from above to urge the filler agent into the pores; or using negative pressure (suction) from below to urge the filler agent into the pores. Alternatively filling the pores comprises adding the filler agent into the pores by the force of gravity, or by several fold enhanced gravity means such as by centrifugation. The same purpose, which is exclusion of growth of cells into at least a portion of the plurality of the pores for at least a portion of the time of culture, can be achieved by using a scaffold material with small pore sizes.

The method can further include inserting the resulting engineered cartilage tissue and support scaffold into a plastic support frame having a semipermeable membrane. The semipermeable membrane has a pore size of about 5 microns or less than about 5 microns, for example about less than about 4 microns, less than about 5 microns, less than about 2.5 microns, less than about 1 micron, less than about 0.5 microns in diameter, for example, less than about 0.4 microns in diameter, of sufficient size to allow flow of medium through the pores. Further, the semipermeable membrane has a pore density of at least about $8 \times 10^5$ pores/cm$^2$, or of some sufficient density to allow flow of medium through the pores.

The membrane composition can be polyethylene terephthalate, polycarbonate, or polytetrafluoroethylene. The growth factor that is present in the culture medium can be a bone morphogenic protein, a transforming growth factor beta, and an insulin-like growth factor, for example the growth factor is insulin-like growth factor-1 (IGF-1), which can be added to the medium to a final concentration of about from 50 ng/ml to about 200 ng/ml. The CM formed by the chondrocytes has a ratio of aggrecan to hyaluronan of about 10:1 to about 500:1, for example, about 20:1, or about 50:1, or about 100:1, or about 150:1. Further, the CM formed by the chondrocytes has a ratio of aggrecan to collagen of about 1:10 to about 10:1, for example, about 2:1, or about 5:1.

Another aspect of the invention is a method for surgical repair of a tissue having a damage, comprising opening the tissue surgically and inserting the in vitro-produced osteochondral tissue directly into the opening. The damage can be acute, partial, or full-thickness chondral injuries, osteochondral injuries, or degenerative processes. The damage can include cartilage defect, osteochondritis dissecans (OCD), osteoarthritis, rheumatoid arthritis, osteonecrosis or any other cartilage lesion.

Also provided is a method for surgical repair of a tissue having damage, involving inserting the in vitro-produced osteochondral tissue arthroscopically. Also provided is a method for treating a joint affected by rheumatoid arthritis or osteoarthritis which involves repairing the joint with the in vitro produced osteochondral tissue implant.

Also provided is a method for surgical repair of a tissue having damage, involving inserting arthroscopically an osteochondral tissue grown independently, and a support scaffold. Also provided is a method for treating a joint affected by rheumatoid arthritis or osteoarthritis which involves repairing the joint with an independently produced osteochondral tissue implant.

Another embodiment of the invention is a kit for producing an osteochondral tissue in vitro, the kit comprising a biocompatible support scaffold, a medium for culture of chondrogenic cells, a container, and instructions for use. The kit may further provide suitable chondrogenic cells for culture. The scaffold contains at least one of the group consisting of natural cancellous bone, demineralized natural cancellous bone, collagen, and bone substitute material. The kit can further include alginate.

An alternative embodiment of the invention is a kit for surgically implanting an osteochondral tissue, the kit comprising a biocompatible support scaffold, an alginate recovered chondrocyte (ARC) tissue comprising chondrogenic cells, a container, and instructions for use. In this embodiment, the ARC tissue in the kit is ready to use for surgical implantation without further culture, or with only minimal culture in vitro.

DETAILED DESCRIPTION OF SPECIFIC EMBODIMENTS

Figure 1:
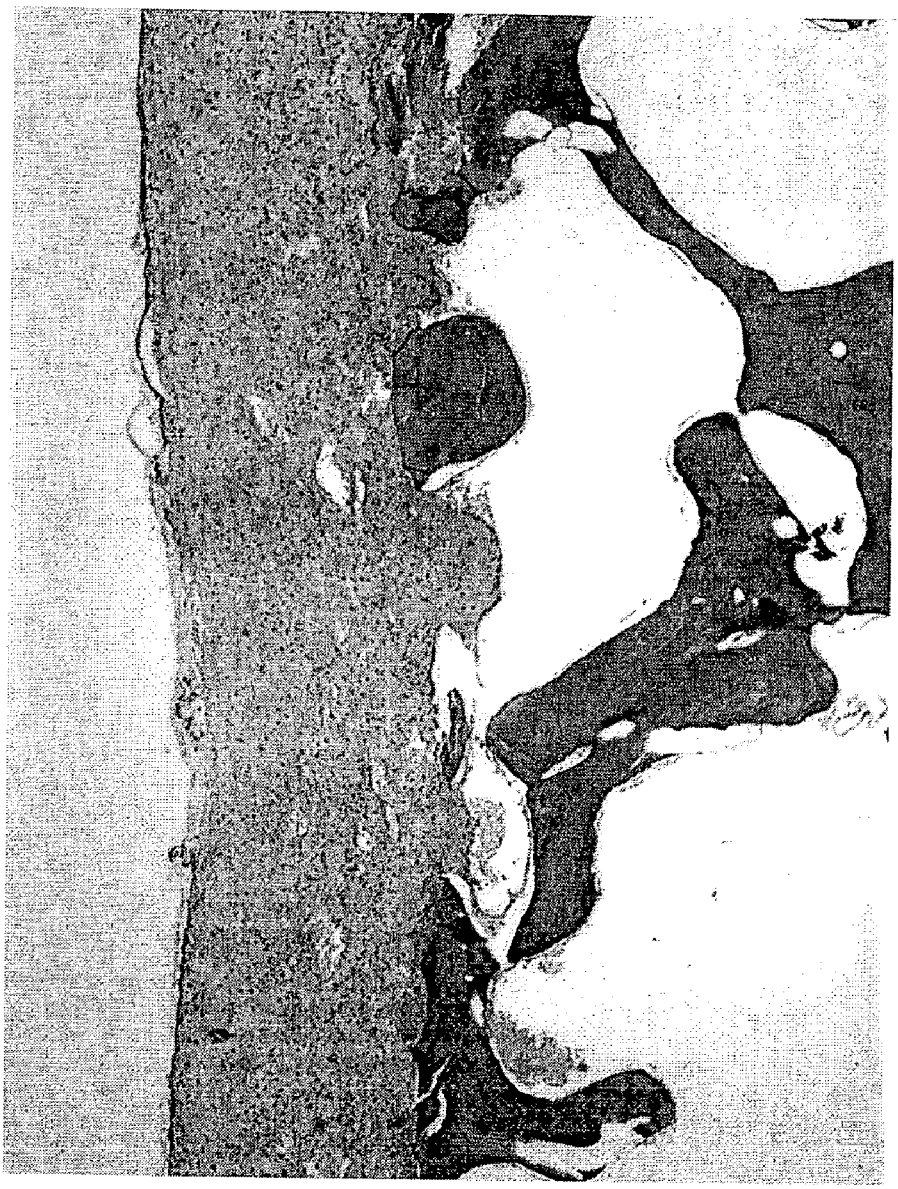
FIG. 1 is a light photomicrograph of a cross section of bovine ARC cartilage tissue grown on top of bovine cancellous bone for two weeks in culture after release from alginate beads, the histology obtained by staining the section with hematoxylin-eosin.

The present invention relates to a transplantable osteochondral implant and a method for its production. The implant includes engineered cartilage tissue attached to a biocompatible support scaffold. In the present methods, an osteochondral implant is produced in vitro by culturing isolated chondrogenic cells for an amount of time effective for the formation of a chondrogenic cell-associated matrix. The chondrogenic cells with cell-associated matrix are previously cultured on a porous biocompatible support scaffold in the presence of a growth factor, for a time effective for allowing both the formation of an engineered cartilage tissue and attachment of the engineered cartilage tissue to the biocompatible support scaffold.

The porous biocompatible support scaffold can be composed of natural cancellous bone, demineralized natural cancellous bone, or bone substitute material such as calcium phosphate, or collagen, or hydroxyapatite or a combination of these materials and is of a thickness of more than 2 mm. For example, the thickness of the support scaffold can be at least about 3 mm, at least about 5 mm, at least about 8 mm, at least about 10 mm or even greater, depending upon the anatomy of the joint into which the implant will be surgically inserted.

The pores of the biocompatible support scaffold or bone substitute material are, in certain embodiments, previously filled with a biocompatible filler agent that causes the chondrogenic cells to remain on top or near to the top of the scaffold material and prevents their infiltration beyond a desired depth in to the pores of the scaffold material. The biocompatible filler agent includes, for example, a purified preparation of hyaluronan, collagen, or alginate, or a combination of each.

The composition of the chondrogenic cell-associated matrix (CM) includes, for example, aggrecan, collagen types II, IX and XI, and hyaluronan. The tissue can include at least about 5 mg/cm$^3$ aggrecan, for example, at least about at least about 7 mg/cm$^3$ aggrecan or at least about 10 mg/cm$^3$ aggrecan. In some embodiments, the ratio of aggrecan to hyaluronan varies from about 10:1 to about 500:1, and the ratio of aggrecan to collagen varies from about 1:10 to about 1:1, and even to about 10:1, depending on the length of time of culture of the tissue and the degree of flexibility or stiffness desired.

Chondrogenic cells used for the production of an oseochondral graft can be isolated from various sources, such as articular cartilage and fibrocartilages. For example, the cells can be isolated from articular cartilage, costal cartilage, nasal cartilage, auricular cartilage, tracheal cartilage, epiglottic cartilage, thyroid cartilage, arytenoid cartilage or cricoid cartilage. Exemplary fibrocartilages include tendon, ligament, meniscus or intervertebral disc.

The in vitro-produced osteochondral tissue provided herein can be used in the surgical repair of tissue. Such damage includes acute full-thickness chondral injuries, osteochondral injuries, and degenerative processes. Surgical repair can include, for example, open surgical techniques (arthrotomy) and arthroscopic applications/insertion of the in vitro-produced tissue.

An effective treatment preferably restores the tissues' ability to distribute mechanical forces. Distribution of mechanical forces is disclosed, for example, in Mizrahi et al., 1986, Biorheol 23:311-330.

The problem of repair of defects in cartilage has been pursued by several approaches, in particular by use of cell-based therapies. These therapies aim to restore the normal tissue function by implanting cells or tissue cultivated in vitro. The implanted cells or tissue are designed to replace the damaged or diseased cells or tissue. In many of these approaches, however, while cells are present, a tissue has not formed.

Accordingly, the invention provides a method for the production of an osteochondral graft, for the repair of those defects that involve both the articular cartilage and the underlying bone. In preferred embodiments, engineered cartilage tissue is attached to a biocompatible support scaffold during the culture process.

Generally, chondrogenic cells are isolated and cultured to produce chondrocytes with a chondrogenic CM. The chondrocytes and their CM are then cultured on a biocompatible support scaffold in the presence of one or more growth factors for a time effective to produce an osteochondral implant.

Isolation of chondrocytes/chondrogenic cells

Chondrogenic cells useful in the present compositions and methods can be isolated from essentially any tissue that contains this type of cell. As used herein and in the claims, the term "chondrogenic cell" means any cell that, when exposed to appropriate stimuli, can differentiate to become capable of producing and secreting components characteristic of cartilage tissue. The chondrogenic cells can be isolated directly from pre-existing cartilage tissue, for example, hyaline cartilage, elastic cartilage, or fibrocartilage. Specifically, chondrogenic cells can be isolated from articular cartilage (from either weight-bearing or non-weight-bearing joints), costal cartilage, nasal cartilage, auricular cartilage, tracheal cartilage, epiglottic cartilage, thyroid cartilage, arytenoid cartilage, cricoid cartilage, tendon, ligament, meniscus and intervertebral discs, either nucleus pulposus or annulus fibrosus. Tendon and ligament cells can also be isolated from a specific source, such as the anterior cruciate ligament or Achilles tendon.

Alternatively, chondrogenic cells can be isolated from bone marrow (See for example, U.S. Pat. Nos. 5,197,985 and 4,642,120; Wakitani et al. (1994) J. Bone Joint Surg. 76:579-591). Chondrogenic cells can also be derived from stem cells (U.S. Pat. No. 6,214,369).

Suitable chondrocytes can be isolated from any suitable mammalian source organism, including, without limitation, human, ape such as orangutan, monkey, chimpanzee, carnivore such as dog, cat, rodent such as rat, mouse, farm animals such as horse, cow, pig, sheep, goat, and zoo animals such as elephants, pandas and giraffes and the like. The methods of treatment herein are suitable for human patients, and for subjects from any of these groups of animals.

Chondrocyte cells are isolated by any suitable method. Various starting materials and methods for chondrocyte isolation are known. See generally, Freshney, Culture of Animal Cells: A Manual of Basic Techniques, 2d ed., A. R. Liss Inc., New York, pp 137-168 (1987); Klagsburn, "Large Scale Preparation of Chondrocytes," Methods Enzymol. 58:560-564 (1979).

If the starting material is a tissue in which chondrocytes are substantially the only cell type present, e.g., articular cartilage, cells can be obtained directly by conventional collagenase digestion and tissue culture methods. Alternatively, cells can be isolated from a tissue having additional cell types present in the starting material. One known method for chondrocyte isolation includes differential adhesion to plastic tissue culture vessels. In a second method, antibodies that bind to chondrocyte cell surface markers can be coated on tissue culture plates and then used selectively to bind chondrocytes from a heterogeneous cell population. In a third method, fluorescence activated cell sorting (FACS) using chondrocyte-specific antibodies is used to isolate chondrocytes. In a fourth method, chondrocytes are isolated on the basis of their buoyant density, by centrifugation through a density gradient comprising a standard gradient forming material such as Ficoll.

If desired, chondrocyte stem cells rather than differentiated chondrocytes can be used. Examples of tissues from which stem cells for differentiation, or differentiated cells suitable for transdifferentiation, can be isolated include placenta, umbilical cord, bone marrow, skin, muscle, periosteum, or perichondrium. Cells are isolated from these tissues by explant culture and/or by enzymatic digestion of surrounding matrix using conventional methods.

In some embodiments, cells isolated as part of the method are genetically modified such that they express an exogenous protein, for example, a full-length protein, a fusion protein, a mutated protein, a truncated protein, or a modified protein such as a phosphorylated protein, or the cells are modified to express an inducer of expression of an endogenous protein. A genetic modification includes the introduction of an exogenous nucleic acid such as DNA, or introduction of an increased amount of an endogenous nucleic acid. The DNA to be incorporated is a construct chosen to achieve expression either of a therapeutic product, a product involved in production of cartilage, or a product capable of relieving a requirement of culture medium, such as a growth factor, a cytokine, or a particular cartilage type.

Cell culture in medium for production of chondrocyte CM

Isolated chondrocytes/chondrogenic cells are suspended at a density of, for example, at least about 10$^4$ cells/ml, for example, about 2×10$^4$ cells/ml, about 4×10$^4$ cells/ml, or about 6×10$^4$ cells/ml, in an appropriate medium. A suitable medium includes agarose or a solution containing sodium alginate. Cells are cultured under conditions effective for maintaining a spherical conformation, which is conducive to production of a membrane-bound CM similar to that found in vivo. Chondrocytes are cultured in alginate for a time period effective for formation of a CM, for example, at least about five days. When chondrocytes are cultured in alginate, they retain their spherical shape (typical of chondrocytes) and maintain a large amount of matrix. The media within which the chondrocytes are cultured can contain a stimulatory agent, such as fetal bovine serum or another heterologous serum, to enhance production of the CM. In some embodiments, the medium can contain autologous serum, which has been prepared from a blood sample previously taken from the intended recipient subject of the surgical implant. Alternatively, serum can be prepared from an isologous source, such as from an identical twin to the subject, or from an animal subject having the same genotype as the animal recipient. Isolation and culture of chondrocytes in alginate for production of transplantable cartilage matrix is shown in U.S. Pat. No. 6,197,061.

In another embodiment, the culture medium for the chondrocytes further includes at least one exogenously added specific growth factor. Addition of a specific growth factor, for example, that is not present in fetal bovine serum, such as a bone morphogenic protein, a transforming growth factor, or an insulin-like growth factor such as IGF-1, can act as an effective stimulator of matrix formation. In this embodiment of the invention, growth factor is added to the medium in an amount effective to obtain near-maximal stimulation formation of cell-associated matrix, and is dependent on the type of cells thus stimulated. Typically for chondrocytes, about 50 ng/ml to about 200 ng/ml of growth factor is used. For ligament, tendon and meniscus cells, an amount up to about 1 µg/ml can be used.

Amplification of chondrocytes or chondrogenic cells in the growth medium does not induce loss of the chondrocyte phenotype, as occurs when amplification is performed in monolayer culture. In a preferred embodiment, a chondrocyte phenotype is one typically observed in articular cartilage, where cells have a spherical shape. In some embodiments, cells additionally have the ability to synthesize and accumulate within the matrix significant amounts of both aggrecan and type II collagen at the same time accumulating within the matrix a minimal amount of type I collagen. A minimal amount of collagen type I means an amount of collagen type I that is less than about 10% of all collagen molecules that become incorporated within the matrix.

An articular cartilage chondrocyte is preferably phenotypically stable. A phenotypically stable articular cartilage chondrocyte retains the ability to effectively incorporate major structural macromolecules into a cartilage-like matrix.

Cells that are phenotypically stable synthesize at least about 10 times more aggrecan than hyaluronan (on a mass basis). Further, the ratio of aggrecan to hyaluronan in the matrix produced by articular chondrocytes can remain greater than about 10.

Chondrocytes with CM

Culture of chondrocytes in alginate results in production of an extracellular matrix (ECM), which is organized into compartments: a CM compartment, which metabolically resembles the pericellular and territorial matrices of native tissues, and a matrix compartment which is further removed from the cells, and which metabolically resembles the interterritorial matrix of native tissue.

The formation of a highly structured CM around each chondrocyte provides several advantages. The CM in vivo is anchored to the cell via receptors such as anchorin CII (which binds to collagen), and CD44 (which binds to hyaluronan in proteoglycan aggregates). Once this matrix has been reestablished in a cell culture, the cells are less likely to become dedifferentiated. Further, the chondrocyte turns over proteoglycan aggrecan, and thus remodels this matrix relatively rapidly.

In preferred embodiments, the CM compartment of the ECM produced during culture in alginate includes aggrecan, collagen types II, IX and XI, and hyaluronan. Aggrecan molecules are formed principally in aggregates bound to receptors (including CD44) on the chondrocyte cell membrane via hyaluronan molecules.

Further, the molecular composition of the CM (around each cell), and the molecular composition of the further removed matrix (between the cells), can be altered by modifying the specific culture conditions. These modifications include the physical arrangement of the culture system, and application of various growth factors. Manipulation of matrix production and organization are used for engineering of articular cartilage in vitro for surgical treatment of cartilage injury.

The collagen content and extent of crosslinking can be varied, depending on the clinical application. Tissues with higher amounts of crosslinking are desirable for simulation of a more mature cartilage. Typically, both the tissue content of collagen and extent of pyridinoline crosslinks in collagen increase with time of culture. The crosslinks in particular show a large increase in concentration after two weeks of culture. During brief culture periods, collagen fibrils in the cell-associated matrix are not excessively crosslinked. In general, a tissue with good functional properties and relatively few crosslinks is easier to manipulate.

In another embodiment, the chondrocytes are isolated from fibrocartilage, either white or yellow (elastic). The chondrocytes retain their fibrocartilage phenotype thus producing a cell-associated matrix having collagen and proteoglycan contents more characteristic of the fibrocartilage source from which they are isolated. In this embodiment, type I collagen can be the predominant collagen type depending upon the tissue desired to be replicated.

Recovery of chondrocytes with CM

Recovery of cultured chondrocytes with a CM can be accomplished by solubilizing alginate beads after an effective culture period, using known techniques. The resulting cell suspension is centrifuged, separating the cells with their CM into the pellet away from components of the further removed matrix which remain in the supernatant.

Culturing the chondrocyte with CM on a biocompatible support scaffold.

Chondrocytes and CM, isolated as described above, are further cultured on a porous biocompatible support scaffold (FIG. 1). In one embodiment, a cell culture insert containing a porous biocompatible support scaffold in a plastic support frame is used to form a culture environment. Culture medium flows around the cell culture insert in both the outer and inner chambers. In this embodiment, the cell culture insert includes a semipermeable membrane. The semipermeable membrane allows medium to flow into the cell culture insert in an amount effective for substantially immersing the chondrocytes and their CM.

The porous biocompatible support scaffold preferably includes at least one of the group of: natural cancellous bone, demineralized natural cancellous bone (see U.S. Pat. No. 5,904,716) a bone substitute material such as calcium phosphate (see U.S. Pat. No. 6,277,151), collagen, and hydroxyapatite. The scaffold can have a thickness of at least about 2 mm, for example, at least about 3 mm, 4 mm, 6 mm or even about 10 mm. In an alternative embodiment, the scaffold can have a thickness of about 1.5 mm or about 10 mm, the thickness of the scaffold being chosen as appropriate to the anatomical properties of the joint to be repaired. A resorbable implant biomaterial made of condensed calcium phosphate particles is shown in U.S. Pat. No. 6,077,989.

The porous biocompatible support scaffold is cut or is formed so that it has a shape and diameter similar to that of the cell culture insert. Further, the porous biocompatible support scaffold can comprise a single piece of material, a composite of multiple materials formed as a single piece of material, or a mosaic of smaller individual pieces assembled to form a single shape.

Prior to seeding the chondrocytes with their cell-associated matrix on top of the porous biocompatible support scaffold, the pores can be filled with a biocompatible filler agent to prevent infiltration of cells into the scaffold material to a depth that is less than or equal to about 1 mm. Some infiltration of cells into the scaffold material (less than or equal to about 1 mm) is associated with attachment of the chondrocytes to the scaffold material. The filler agent comprises at least one of a purified preparation of hyaluronan, a collagen, or an alginate. Alternatively, the pore size of materials comprising the scaffold is sufficiently small so that cell infiltration to greater than a depth of about 1 mm is substantially retarded.

The semipermeable membrane allows for diffusion of the biocompatible filler agent away from the chondrocytes, and for diffusion of culture medium towards the chondrocytes, to provide access to nutrients and substantial decrease in amount of waste products in the vicinity of the cells. The membrane preferably has a pore size that substantially prevents rapid diffusion of the biocompatible filler agent out of the scaffold material through the pores. For some embodiments, the membrane has a pore size that is less than or equal to about 5 microns. Further, the membrane preferably has a pore density that provides sufficient strength so that the membrane can be removed from the culture frame without curling and also provides sufficient strength so that the tissue on the membrane can be manipulated and cut to a desired size. In an exemplary embodiment, the membrane has a pore density of at least about $8 \times 10^5$ pores/cm$^2$.

The membrane can be made of any material suitable for use in culture. Examples of suitable membrane systems include, without limitation: Falcon Cell Culture Insert (Polyethylene terephthalate (PET) membrane, pore size about 0.4 microns to about 3 microns, diameter 12 mm to about 25 mm); Coaster Transwell Plate (Polycarbonate membranes, pore size, about 0.1 microns to about 5.0 microns, diameter about 12 mm to about 24.5 mm); Nunc Tissue Culture Insert (Polycarbonate Membrane Insert: pore size, about 0.4 microns to about 3.0 microns, diameter about 10 mm to about 25 mm); and Millicell Culture Plate Insert (Polytetrafluoroethylene (PTFE) membrane, polycarbonate, pore size about 0.4 microns to about 3.0 microns, diameter about 27 mm).

Chondrocytic cells are cultured in a suitable growth medium, for example, a medium that includes about equal parts of Dulbecco's modified Eagle medium and Ham's F12 medium, further comprising about 20% fetal bovine serum (Hyclone, Logan, Utah), about 25 µg/ml ascorbate, and an antibiotic, such as about 50 µg/ml gentamicin (Gibco). In a related embodiment, cells are cultured in a closed chamber that allows for continuous pumping of medium. The medium contains fetal bovine serum including endogenous insulin-like growth factor-1 (IGF-1), at a concentration for example of at least about 10 ng/ml. In this embodiment, fetal bovine serum can also be considered a growth factor. One or more additional suitable growth factors can be added exogenously to the medium to stimulate formation of the cell-associated matrix. Such optional growth factors include, without limitation, one or more of any growth factor that stimulates matrix synthesis by chondrocytes, for example, a bone morphogenetic protein, a transforming growth factor such as TGFβ, and an insulin-like growth factor, for example, IGF-1.

Figure 2:
FIG. 2 is a photograph of a top view of a bovine ARC cartilage tissue osteochondral implant, two weeks in culture after release from alginate beads, juxtaposed on a conventional ruler, to indicate the actual size of the implant.
Figure 3:
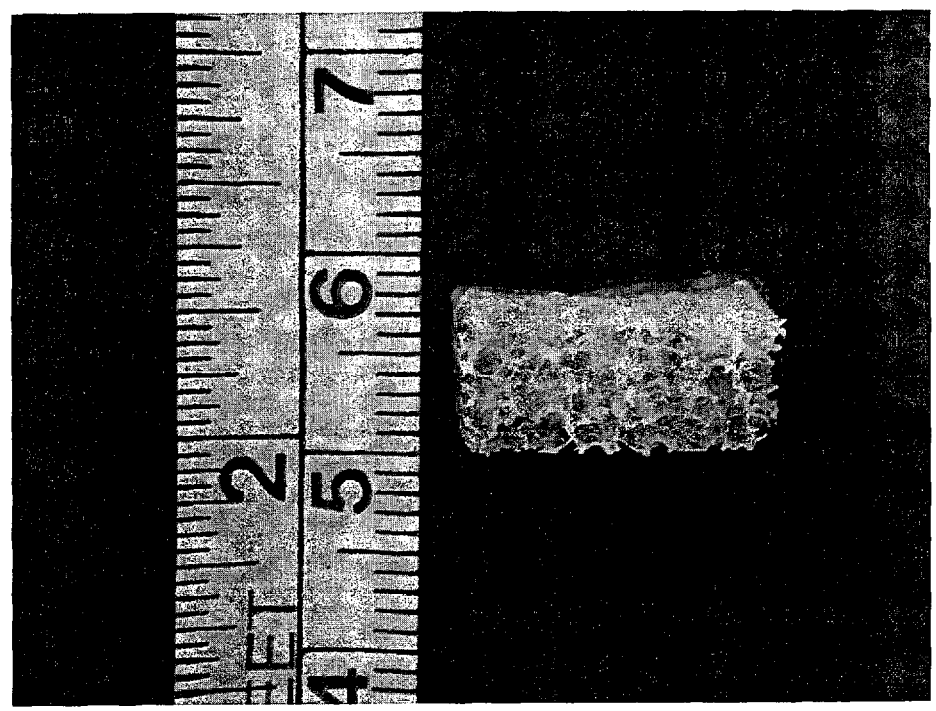
FIG. 3 is a photograph of a side view of a bovine ARC cartilage tissue osteochondral implant, two weeks in culture after release from alginate beads, juxtaposed on a conventional ruler, to indicate the actual size of the implant.

In another aspect of the invention, cells with a reestablished CM are further cultured in medium on the biocompatible support scaffold for a length of time effective for allowing formation of a cohesive cartilage matrix. An effective time of culture is typically at least about 3 days under standard culture conditions. Partial inhibition of matrix maturation prior to implantation can provide a matrix that is not as stiff as a mature cartilage, and which has a tensile strength sufficient to retain its shape and structure during handling (FIGS. 2 and 3).

In an additional step, an osteochondral implant can be removed from the tissue culture insert after a period of at least about 3 days, or at a further time at which the cartilage tissue has sufficiently matured to allow handling. Removal from the culture insert allows efficient removal of the biocompatible filler agent, if present, from within the pores of the scaffold, and allows effective diffusion of nutrients to the cartilage tissue and effective diffusion of waste products away from the cartilage tissue. The osteochondral implant can remain in the culture until a desired maturity for surgical implantation has been achieved.

It is within the embodiments of the present invention to have one, two or more layers of cartilage tissue, using methods that are described in U.S. patent application 2003/0077821 A1. Cells can be obtained from different layers of cartilage as appropriate, or can be cultured as a monolayer such that two or more monolayers are used to reconstitute a stratified cartilage tissue.

Cartilage matrix

In general, the cartilage matrix that forms on the biocompatible support scaffold has a concentration of aggrecan of at least about 5 mg/cm$^3$, and includes an amount of hyaluronan effective for allowing newly synthesized molecules to be incorporated into proteoglycan aggregates. The engineered cartilage used in the present methods closely resembles naturally occurring articular cartilage in its physicochemical properties, and can be produced in a short period of time, typically about 14 days. The engineered cartilage can be removed from the semipermeable membrane.

The foregoing invention having been fully described, it is further exemplified by the following claims, which are not to be construed as limiting. The entire contents of any citations herein are hereby incorporated in entirety by reference.

What is claimed is:

1. A method for producing in vitro a transplantable osteochondral implant the method comprising:
   culturing chondrogenic cells in vitro in alginate beads such that the cells develop a membrane-bound cell associated matrix comprising at least one of aggrecan, collagen types II, IX and XI, and hyaluronan;
   solubilizing the alginate beads to form a suspension comprising the cultured cells with the membrane-bound cell associated matrix;
   centrifuging the suspension to separate the cultured cells with the membrane-bound cell associated matrix from an extracellular matrix compartment that is further removed from the cells;
   recovering the cultured cells with the membrane-bound cell associated matrix;
   providing a biocompatible support scaffold, wherein the support scaffold consists of at least one of calcium phosphate and hydroxyapatite, the support scaffold having a plurality of pores, a top surface and a bottom surface, wherein pores associated with the bottom surface of the support scaffold are filled with a biocompatible filler agent comprising at least one selected from the group consisting of purified hyaluronan, collagen, and alginate;

seeding the cultured chondrogenic cells with the membrane-bound cell associated matrix on the top surface of the support scaffold as a phenotypically stable culture such that the cells attach to the support scaffold; and further culturing the seeded cells on the support scaffold in the presence of culture medium, such that the cells seeded on the top surface of the scaffold infiltrate into pores associated with the top surface of the support scaffold, yet the biocompatible filler agent substantially prevents infiltration of the cells into pores associated with the bottom surface, thereby forming a cohesive cartilage matrix in a layer on top of the support scaffold of the bone substitute material.

2. The method of claim 1, wherein the pores of the biocompatible support scaffold are filled with the biocompatible filler agent prior to the seeding step.

3. The method of claim 1, wherein the culture medium comprises a growth factor selected from the group consisting of a bone morphogenic protein, a transforming growth factor, and an insulin-like growth factor.

4. The method of claim 1, wherein the culture medium comprises insulin-like growth factor-1 (IGF-1).

5. The method of claim 4, wherein IGF-1 is present at about 50 ng/ml to about 200 ng/ml.

6. The method of claim 1, wherein the membrane-bound cell associated matrix has a ratio of aggrecan to hyaluronan of about 10:1 to about 200:1.

7. The method of claim 1, wherein the membrane-bound cell associated matrix has a ratio of aggrecan to collagen of about 1:10 to about 10:1.

8. A transplantable osteochondral implant product comprising engineered cartilage tissue attached to a biocompatible support scaffold, wherein the support scaffold is bone substitute material consisting of at least one of calcium phosphate and hydroxyapatite, the support scaffold having a plurality of pores, a top surface and a bottom surface, wherein pores associated with the bottom surface of the support scaffold are filled with a biocompatible filler agent comprising at least one selected from the group consisting of purified hyaluronan, collagen, and alginate, and wherein the implant is made by the process comprising:

culturing chondrogenic cells in vitro in alginate beads such that the cells develop a membrane-bound cell associated matrix comprising at least one of aggrecan, collagen types II, IX and XI, and hyaluronan;

solubilizing the alginate beads to form a suspension comprising the cultured cells with the membrane-bound cell associated matrix;

centrifuging the suspension to separate the cultured cells with the membrane-bound cell associated matrix from an extracellular matrix compartment that is further removed from the cells;

recovering the cultured cells with the membrane-bound cell associated matrix;

seeding the cultured chondrogenic cells with the membrane-bound cell associated matrix on the top surface of the support scaffold as a phenotypically stable culture such that the cells attach to the support scaffold; and further culturing the seeded cells on the support scaffold in the presence of culture medium, such that the cells seeded on the top surface of the scaffold infiltrate into pores associated with the top surface of the support scaffold, while the biocompatible filler agent substantially prevents infiltration of the cells into pores associated with the bottom surface of the support scaffold.

9. The implant of claim 8, wherein the bone substitute material has a thickness of at least 2 mm.

10. The implant of claim 8, wherein the cartilage tissue comprises at least 5 mg/cm$^3$ aggrecan.

11. The implant of claim 10, wherein the cartilage tissue comprises collagen and wherein the ratio of aggrecan to collagen is from about 1:10 to about 10:1.

12. The implant of claim 8, wherein the cartilage tissue comprises aggrecan and hyaluronan and wherein the ratio of aggrecan to hyaluronan in the tissue is from about 10:1 to about 500:1.

13. The implant of claim 8, wherein the pores associated with the bottom surface of the support scaffold are filled with the biocompatible filler agent prior to seeding the cells.

14. The implant of claim 13, wherein the process further comprises including culture medium in the pores of the support scaffold such that cell growth extends into the pores associated with the top surface while the biocompatible filler agent substantially prevents cell infiltration into the pores associated with the bottom surface.

15. The implant of claim 13, wherein the biocompatible filler agent comprises a high viscosity liquid or a gel.

16. The implant of claim 8, wherein chondrogenic cells are cultured in vitro in the presence of a removable semi-permeable membrane filter.

17. The implant of claim 8, wherein the chondrogenic cells are isolated from an articular cartilage or a fibrocartilage.

18. The implant of claim 17, wherein the chondrogenic cells are from a fibrocartilage selected from the group consisting of: costal, nasal, auricular, tracheal, epiglottic, thyroid, arytenoid and cricoid cartilages.

19. The implant of claim 17, wherein the fibrocartilage is selected from the group of tendon, ligament, meniscus and intervertebral disc.

20. The implant of claim 8, wherein the chondrogenic cells are differentiated chondrocytes or chondrogenic stem cells.

21. The implant of claim 20, wherein the chondrogenic stem cells are stem cells from a tissue selected from the group consisting of placenta, umbilical cord, bone marrow, skin, muscle, periosteum, fat, and perichondrium.

22. A method for treating a patient by surgical repair of a tissue having a damage, the method comprising opening the tissue surgically and inserting the in vitro-produced osteochondral tissue of claim 8 directly into the opening.

23. The method of claim 22, wherein the damage is selected from the group consisting of: acute chondral injuries, full-thickness chondral injuries, partial chondral injuries, and osteochondral injuries.

24. A method for treating a patient by surgical repair of a tissue having damage, comprising inserting the in vitro-produced osteochondral tissue of claim 8 arthroscopically.

25. A method for treating a patient having a joint affected by osteoarthritis, rheumatoid arthritis, osteochondritis dissecans, osteonecrosis or other cartilage lesion, the method comprising repairing the joint with the in vitro produced osteochondral tissue implant of claim 8.

26. A transplantable osteochondral implant comprising engineered cartilage tissue attached to a biocompatible support scaffold, wherein the support scaffold is a bone substitute material consisting of at least one of calcium phosphate and hydroxyapatite, the support scaffold having a top surface, a bottom surface, and a plurality of pores, wherein the pores of the support scaffold form a gradient of increasing size from the top surface to the bottom surface, and wherein the cartilage tissue is located overlying the top surface of the support scaffold and infiltrates into the pores associated with the top surface of the support scaffold; and wherein the cartilage tissue is produced by culturing a phenotypically stabilized culture of chondrogenic cells having a cell associated matrix comprising at least one of aggrecan, collagen types II, IX and XL, on the top surface of the biocompatible support structure, the chondrogenic cells with the cell associated matrix being obtained by culturing chondrogenic cells in vitro in alginate beads under conditions whereby the cells maintain a spherical conformation and form a membrane-bound cell associated matrix, solubilizing the alginate beads, centrifuging the cells and recovering the cells together with the cell associated matrix;

and further comprising a biocompatible filler agent present in the pores associated with the bottom surface of the support scaffold, wherein the biocompatible filler agent is effective to substantially prevent infiltration of cells into the pores associated with the bottom surface during culture of the engineered cartilage tissue, the biocompatible filler agent comprises at least one selected from the group consisting of purified hyaluronan, collagen, or alginate.

27. The implant of claim 26, wherein the pores associated with the bottom surface are larger than the pores associated with the top surface and wherein the pores associated with the bottom surface are filled with the biocompatible filler agent prior to attaching the chondrogenic cells.

28. The implant of claim 26, wherein following growth of cells, the biocompatible filler is removed by diffusion out of the support scaffold.

* * * * *